(12) United States Patent
Kerr et al.

(10) Patent No.: US 8,292,886 B2
(45) Date of Patent: Oct. 23, 2012

(54) APPARATUS, SYSTEM, AND METHOD FOR PERFORMING AN ELECTROSURGICAL PROCEDURE

(75) Inventors: Duane E. Kerr, Loveland, CO (US); Jeffrey R. Townsend, Loveland, CO (US); William H. Nau, Jr., Longmont, CO (US); Terrence R. Young, Erie, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 579 days.

(21) Appl. No.: 12/574,001

(22) Filed: Oct. 6, 2009

(65) Prior Publication Data
US 2011/0082457 A1 Apr. 7, 2011

(51) Int. Cl.
*A61B 18/14* (2006.01)
(52) U.S. Cl. ............................................ 606/48; 606/51
(58) Field of Classification Search ................ 606/45–52
See application file for complete search history.

(56) References Cited

U.S. PATENT DOCUMENTS

| | | | |
|---|---|---|---|
| 5,389,098 A | 2/1995 | Tsuruta et al. | |
| 5,403,312 A | 4/1995 | Yates et al. | |
| 5,582,611 A | 12/1996 | Tsuruta et al. | |
| 5,722,421 A | 3/1998 | Francese et al. | |
| 5,735,848 A | 4/1998 | Yates et al. | |
| 5,807,393 A | 9/1998 | Williamson, IV et al. | |
| 5,810,811 A | 9/1998 | Yates et al. | |
| 5,833,690 A | 11/1998 | Yates et al. | |
| 6,004,335 A | 12/1999 | Vaitekunas et al. | |
| H1904 H | 10/2000 | Yates et al. | |
| H2037 H | 7/2002 | Yates et al. | |
| 6,626,901 B1 | 9/2003 | Treat et al. | |
| 6,860,880 B2 | 3/2005 | Treat et al. | |
| 2003/0069571 A1 | 4/2003 | Treat et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |

(Continued)

OTHER PUBLICATIONS

U.S. Appl. No. 12/176,679, filed Jul. 21, 2008.

(Continued)

*Primary Examiner* — Linda Dvorak
*Assistant Examiner* — Amanda Scott

(57) ABSTRACT

A bipolar forceps includes a shaft extending from a housing and includes an end effector assembly at its distal end. The end effector assembly has a pair of jaw members movable between an open position and a closed position. A knife assembly includes a cutter having a generally circular cross-section. The cutter is configured to cut tissue when the jaw members are in the closed position. One or more electrically conductive tissue sealing plates are disposed on each of the jaw members. The tissue sealing plates are adapted to connect to an electrosurgical energy source configured to deliver electrosurgical energy to tissue held between the jaw members to effect a tissue seal. An actuator is operably coupled to the knife assembly and is configured to selectively reciprocate the cutter relative to the jaw members.

7 Claims, 7 Drawing Sheets

FOREIGN PATENT DOCUMENTS

| | | |
|---|---|---|
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 0 875 209 | 11/1998 |
| EP | 0 878 169 | 11/1998 |
| EP | 1159926 | 12/2001 |
| EP | 1 530 952 | 11/2004 |
| EP | 1 486 177 | 12/2004 |
| EP | 1 649 821 | 10/2005 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report Ep 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

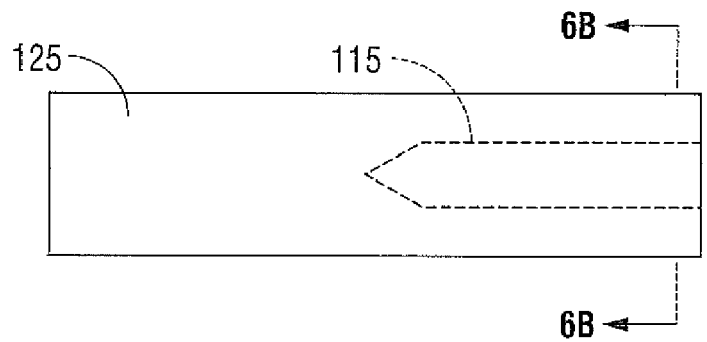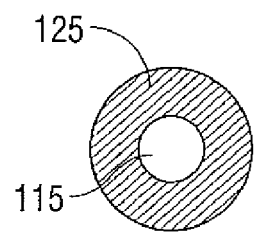
FIG. 6A
FIG. 6B
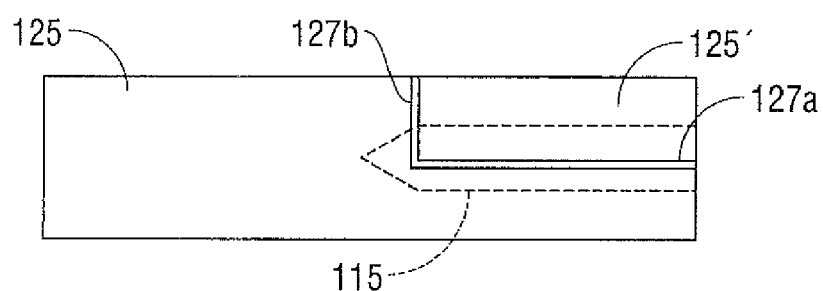
FIG. 6C
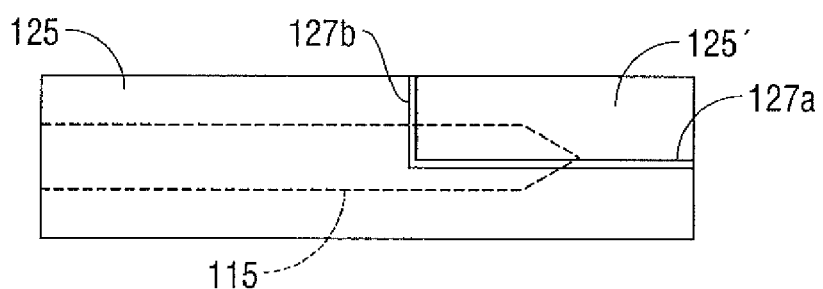
FIG. 6D

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopic forceps for remotely accessing organs through smaller, puncture-like incisions. As a direct result thereof, patients tend to benefit from less scarring and reduced healing time. Typically, the forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of electrosurgical instruments.

SUMMARY

According to an embodiment of the present disclosure, a bipolar forceps includes a shaft extending from a housing and includes an end effector assembly at its distal end. The end effector assembly has a pair of jaw members movable between an open position and a closed position. A knife assembly includes a cutter having a generally circular cross-section. The cutter is configured to cut tissue along the tissue seal when the jaw members are in the closed position. One or more electrically conductive tissue sealing plates are disposed on each of the jaw members. The tissue sealing plates are adapted to connect to an electrosurgical energy source configured to deliver electrosurgical energy to tissue held between the jaw members to effect a tissue seal. An actuator is operably coupled to the knife assembly and is configured to selectively reciprocate the cutter relative to the jaw members to divide tissue.

According to another embodiment of the present disclosure, a bipolar forceps includes a shaft extending from a housing and including an end effector assembly at its distal end. The end effector assembly has a pair of jaw members movable between an open position wherein the jaw members are disposed in spaced relation relative to each other and a closed position wherein the jaw members cooperate to grasp tissue. The forceps also includes a knife assembly including a cutter having a generally circular cross-section. The cutter is configured to cut the tissue when the jaw members are in the closed position. The forceps also includes one or more electrically conductive tissue sealing plates disposed on each of the jaw members. The electrically conductive tissue sealing plates are adapted to connect to an electrosurgical energy source and are configured to deliver electrosurgical energy to tissue held between the jaw members to effect a tissue seal. The forceps also includes a knife channel disposed through at least one of the jaw members. The cutter is configured to reciprocate within the knife channel when the jaw members are in the closed position to divide tissue grasped between the jaw members. An actuator is operably coupled to the knife assembly and is configured to selectively reciprocate the cutter through the knife channel.

According to another embodiment of the present disclosure, a method for performing an electrosurgical procedure includes the step of providing an electrosurgical apparatus. The electrosurgical apparatus includes a shaft extending from a housing. The shaft includes an end effector assembly at its distal end. The end effector assembly has a pair of jaw members movable between an open position and a closed position. The electrosurgical apparatus also includes a knife assembly. The knife assembly includes a cutter having a generally circular cross-section. The cutter is configured to cut tissue along the tissue seal when the jaw members are in the closed position. One or more electrically conductive tissue sealing plates are disposed on each of the jaw members. The tissue sealing plates are adapted to connect to an electrosurgical energy source configured to deliver electrosurgical energy to tissue held between the jaw members to effect a tissue seal. The electrosurgical apparatus also includes an actuator operably coupled to the knife assembly. The actuator is configured to selectively reciprocate the cutter relative to the jaw members to divide tissue. The method also includes the step of delivering electrosurgical energy from the electrosurgical energy source to the electrically conductive tissue sealing plates to achieve a desired tissue effect. The method also includes the step of actuating the cutter to selectively separate the effected tissue from the rest of the effected tissue.

According to another embodiment of the present disclosure, a method of manufacturing a jaw member of an electrosurgical apparatus includes the steps of drilling a channel through the longitudinal thickness of a substantially cylindrical workpiece and making a longitudinal cut through a portion of the workpiece to substantially bisect the channel along at least a portion of the length thereof. The method also includes the step of making a cross-sectional cut through a portion of the workpiece to intersect the longitudinal cut to facilitate removal of a section defined by the intersecting cuts from the workpiece.

BRIEF DESCRIPTION OF THE DRAWING

Various embodiments of the present disclosure are described hereinbelow with references to the drawings, wherein:

FIG. 6A is side view of a workpiece according to an embodiment of the present disclosure;

FIG. 6B is a cross-sectional view taken along section line 6B-6B of FIG. 6A;

FIGS. 6C and 6D are side views of the workpiece of FIG. 6A;

DETAILED DESCRIPTION

Figure 1:
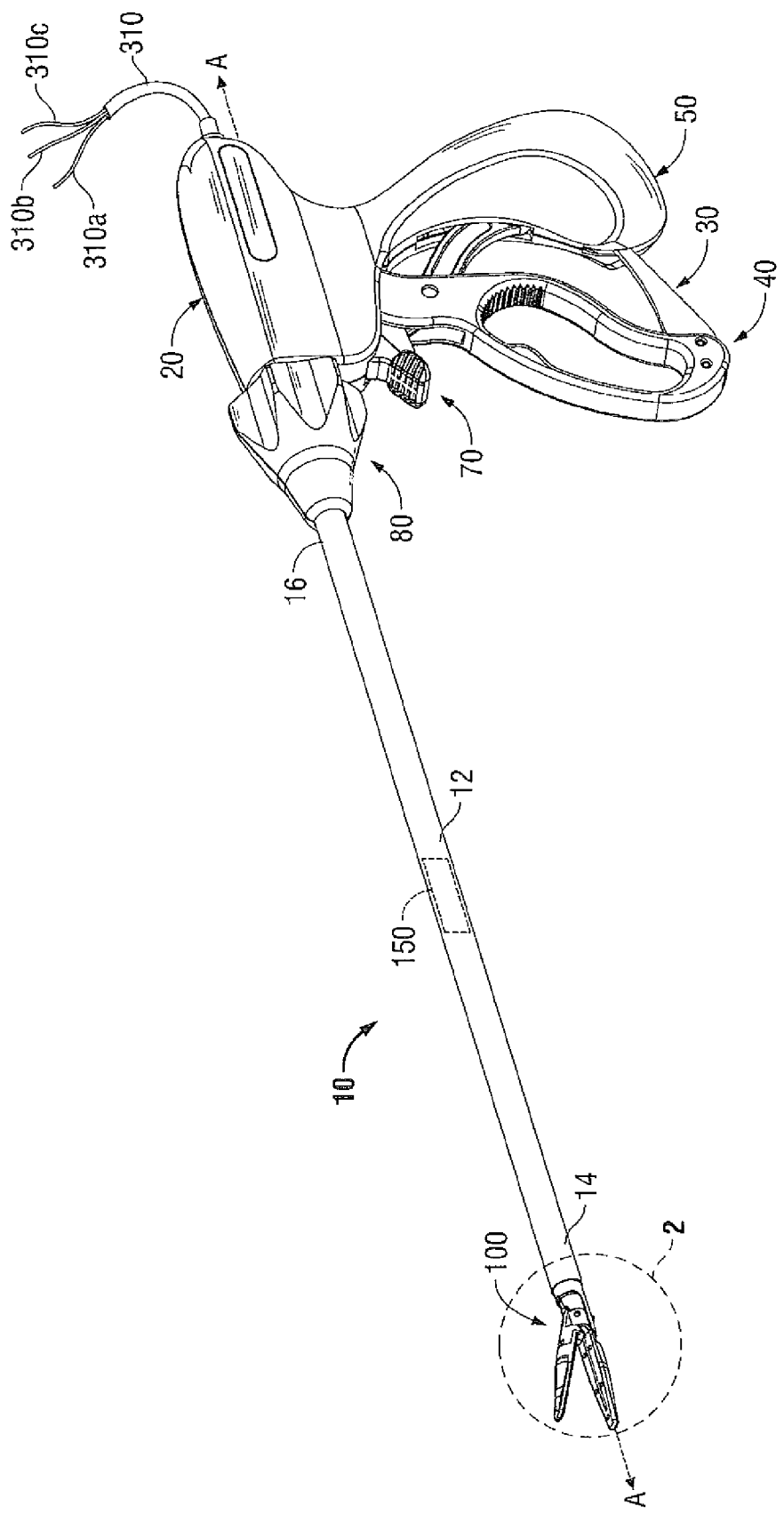
FIG. 1 is a right perspective view of an endoscopic bipolar forceps showing a housing, a shaft, and an end effector assembly in accordance with the present disclosure.

Embodiments of the presently disclosed apparatus are described in detail below with reference to the drawings wherein like reference numerals identify similar or identical elements in each of the several views. In the discussion that follows, the term "proximal" or "trailing" will refer to the portion of a structure that is closer to a user, while the term "distal" or "leading" will refer to the portion of the structure that is farther from the user.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaws from an open to a closed configuration that forms a closed loop electrical circuit such that a desired tissue effect (e.g., a tissue seal) may be achieved.

The electrosurgical forceps includes a knife assembly incorporating a cutter having a generally circular cross-section. The cutter may be, for example, wire, tubing, rod, hypodermic tubing, hypodermic needle, or the like. The cutter is operably coupled at a proximal end to the drive assembly and/or an actuator and includes a distal end having any one of various geometries and/or dimensions configured to divide tissue, as discussed in further detail below.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. Forceps 10 includes a shaft 12 that has a distal end 14 dimensioned to mechanically engage the end effector assembly 100 and a proximal end 16 that mechanically engages the housing 20. For the purposes herein, the forceps 10 is described in terms of a laparoscopic instrument, however, it is contemplated that an open version of the forceps may also include the same or similar operating components and features as described below.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033,399 entitled "ELECTROSURGICAL GENERATOR WITH ADAPTIVE POWER CONTROL". Cable 310 is internally divided into cable leads 310a, 310b, and 310c, that are designed to transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly owned patent Publication No., 2003-0229344, filed on Feb. 20, 2003, entitled VESSEL SEALER AND DIVIDER AND METHOD OF MANUFACTURING THE SAME.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A-A" (See FIG. 1).

As mentioned above, end effector assembly 100 is attached at the distal end 14 of shaft 12 and includes a pair of opposing jaw members 110 and 120. Movable handle 40 of handle assembly 30 is operatively connected to a drive assembly 150 (shown in phantom) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, drive assembly 150 may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

As shown best in FIGS. 2 and 3A-3D, the end effector assembly 100 includes opposing jaw members 110 and 120 that cooperate to effectively grasp tissue for sealing purposes. The end effector assembly 100 may be designed as a unilateral assembly, i.e., jaw member 120 is fixed relative to the shaft 12 and jaw member 110 pivots about a pivot pin 103 relative to jaw member 120 to grasp tissue, or as a bilateral assembly, i.e., jaw members 110 and 120 pivot about pivot pin 103 relative to each other to grasp tissue. In some embodiments, jaw members 110, 120 are operably coupled to each other about a pivot pin 103 that allows jaw member 110 to pivot relative to stationary jaw member 120.

In some embodiments, the pivoting jaw member 110 is actuated by the drive assembly 150 such that distal movement of drive assembly 150 pivots jaw member 110 relative to jaw member 120 to an open position wherein the jaw members 110, 120 are in spaced relation relative to each other and proximal movement of drive assembly 150 pivots jaw member 110 relative to jaw member 120 to a closed position to grasp tissue therebetween. In another embodiment, pivot pin 103 is configured to slide within a cam slot (not shown) to pivot jaw member 110 between the open and closed positions.

Figure 2:
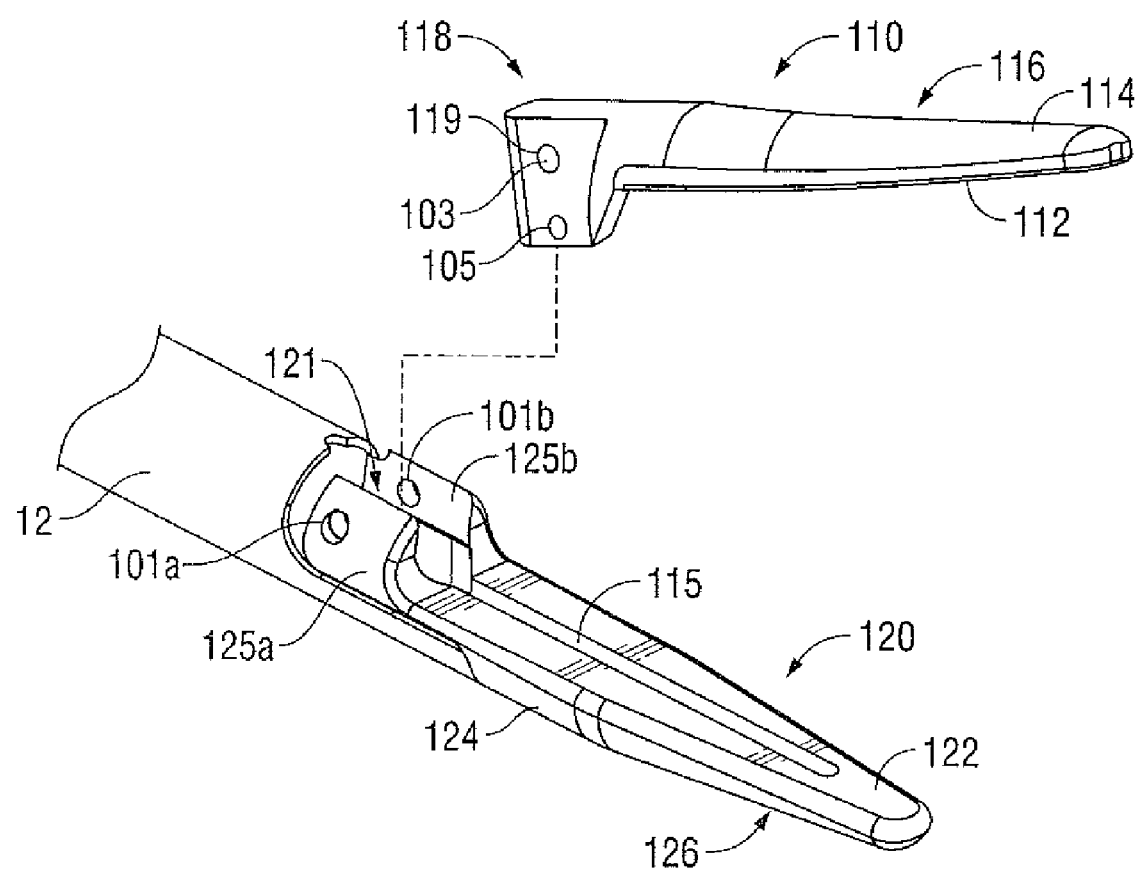
FIG. 2 is an enlarged, right perspective view of the end effector assembly of FIG. 1.

As best shown in FIG. 2, jaw member 110 also includes a jaw housing 116 that has an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 are configured to limit and/or reduce many of the known undesirable effects related to tissue sealing, e.g., flashover, thermal spread and stray current dissipation. In other embodiments, the jaw members 110 and 120 may be manufactured from a ceramic-like material and the electrically conductive surface(s) 112 are coated onto the ceramic-like jaw members 110 and 120.

Jaw member 120 includes similar elements to jaw member 110 such as jaw housing 126 having an insulator 124 and an electrically conductive sealing surface 122 that is dimensioned to securely engage the insulator 124.

As best shown in FIGS. 2 and 3A-3D, a knife channel 115 is defined through the center of jaw member 120. As best shown in the cross-sections of FIGS. 3B and 3D, knife channel 115 may be substantially semi-circular in shape and configured to accommodate a cutter 132 therethrough. As best shown in FIGS. 3A-3D, cutter 132 includes a generally circular cross-section and is configured to advance along knife channel 115 such that at least a portion of the cross-section of cutter 132 is disposed outside of knife channel 115 between jaw members 110 and 120. Activation of cutter 132 is caused by an actuator such as, for example, trigger assembly 70 and/or handle assembly 30. When activated, the cutter 132 advances through knife channel 115 to progressively and selectively divide tissue along a tissue plane in a manner to effectively and reliably divide the tissue. In some embodiments, forceps 10 may be configured such that cutter 132 may only be advanced through knife channel 115 to cut tissue when jaw members 110, 120 are in the closed position to prevent accidental or premature activation of cutter 132 through tissue. In embodiments, tissue grasped between jaw members 110, 120 need not be sealed for cutter 132 to be utilized to divide such tissue. That is, it is not necessary to perform the step of cutting tissue subsequent to or prior to the step of sealing tissue. Likewise, nor is it necessary to perform the step of sealing tissue subsequent to or prior to the step of cutting tissue. For example, tissue may be sealed but not cut. Likewise, tissue may be cut and not sealed.

By way of example, cutter 132 may be a solid wire, a tube (e.g., hypodermic tubing), a rod, a hollow hypodermic needle, a flexible metal, spiral-cut wire, etc.

Figure 3A:
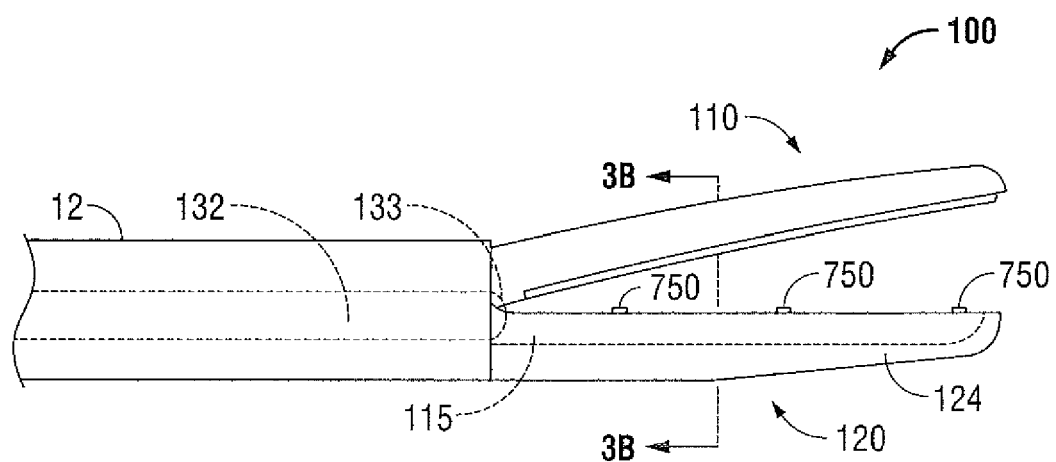
FIGS. 3A and 3C are enlarged, side views of the end effector assembly of FIG. 1.
Figure 3B:
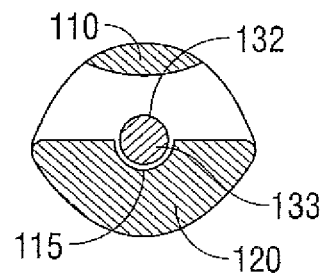
FIGS. 3B and 3D are cross-sectional views taken along section lines 3B-3B and 3D-3D of FIGS. 3A and 3C, respectively.
Figure 3C:
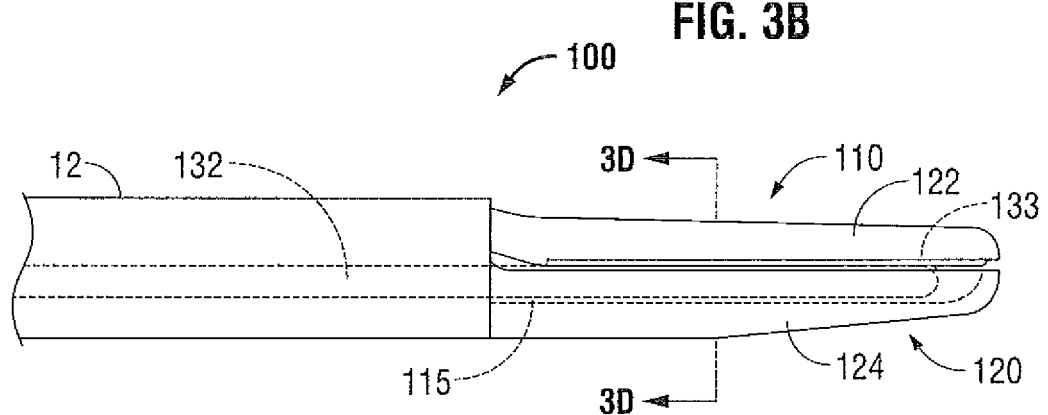
Figure 3D:
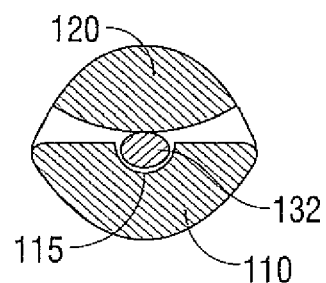
Figure 4A:
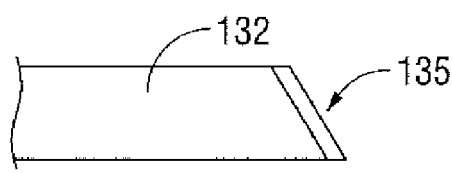
FIG. 4A is a side view of a cutter according to an embodiment of the present disclosure.
Figure 4B:
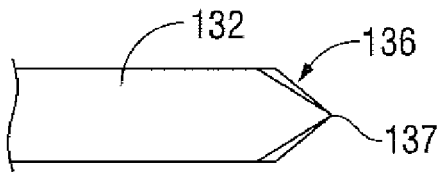
FIG. 4B is a side view of a cutter according to another embodiment of the present disclosure.

In the illustrated embodiment of FIGS. 3A and 3C, cutter 132 includes a substantially blunt tip 133. In other embodiments, cutter 132 may include various geometries and/or distal tips to facilitate reliable division of tissue. More specifically, FIG. 4A shows one embodiment of cutter 132 having an angled distal tip 135 that forms a chisel-type configuration. In yet another embodiment, FIG. 4B shows cutter 132 having a tapered distal end 136 that extends distally to a sharpened distal tip 137. Other distal tip geometries and/or configurations are contemplated and the above embodiments should not be construed as exhaustive.

Figure 5A:
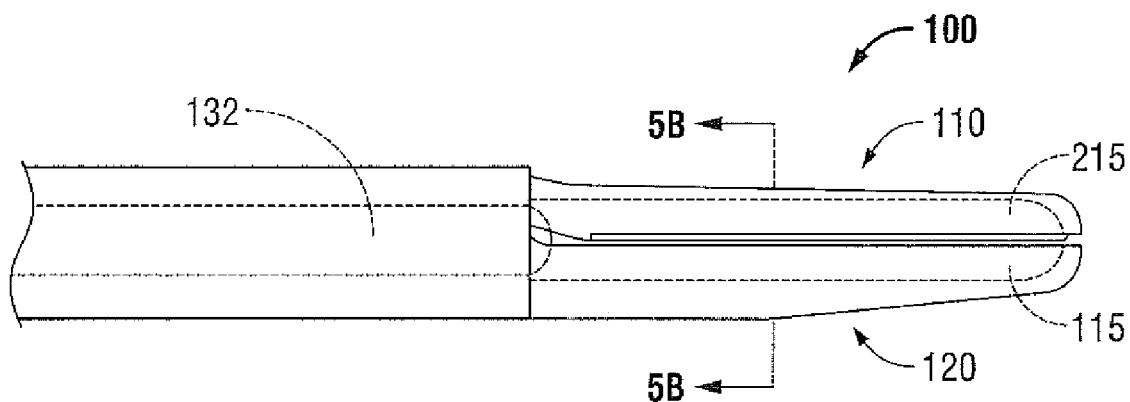
FIG. 5A is an enlarged, side view of the end effector assembly of FIG. 1 according to an embodiment of the present disclosure.
Figure 5B:
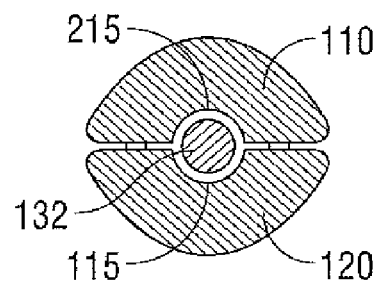
FIG. 5B is a cross-sectional view taken along section line 5B-5B of FIG. 5A.

In another embodiment shown in FIGS. 5A and 5B, jaw member 110 may also include a knife channel 215 that substantially aligns with knife channel 115 of jaw member 120 such that each of knife channels 115 and 215 receive at least a portion of the cross-section of cutter 132 upon advancement therethrough. In this manner, the generally circular cross-section of cutter 132 is accommodated within both knife channels 115 and 215 upon advancement therethrough to aid in aligning the jaw members 110, 120 during cutting of tissue grasped therebetween.

Figure 5C:
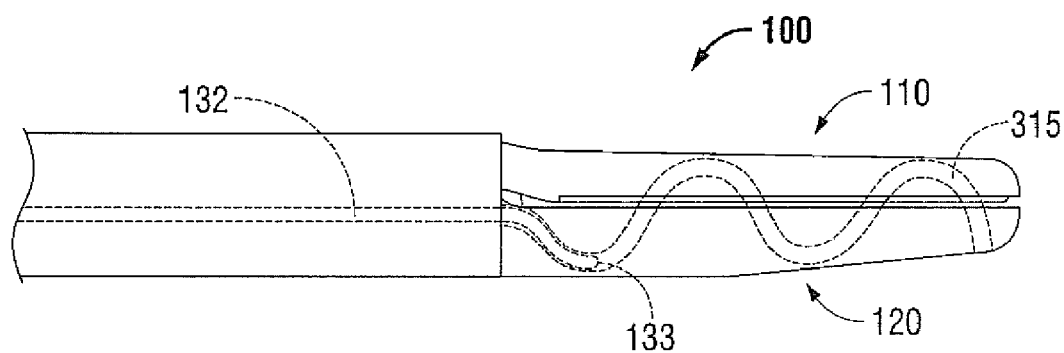
FIG. 5C is an enlarged, side view of the end effector assembly of FIG. 1 according to another embodiment of the present disclosure.

The generally circular cross-section of cutter 132 makes it possible for cutter 132 to advance or snake through various configurations of channels. With this purpose in mind, end effector 100 may include a helical knife channel 315, as shown in the embodiment of FIG. 5C. More specifically, knife channel 315 is spirally defined through both jaw members 110, 120 continuously, such that cutter 132 may be advanced through knife channel 315 in a helical-like manner to progressively and selectively divide tissue along a tissue plane. In this scenario, activation of cutter 132 (e.g., via trigger assembly 70 and/or handle assembly 30) may cause cutter 132 to be advanced distally while being simultaneously rotated about its longitudinal axis to aid in the helical-like advancement through knife channel 315.

Figure 5D:
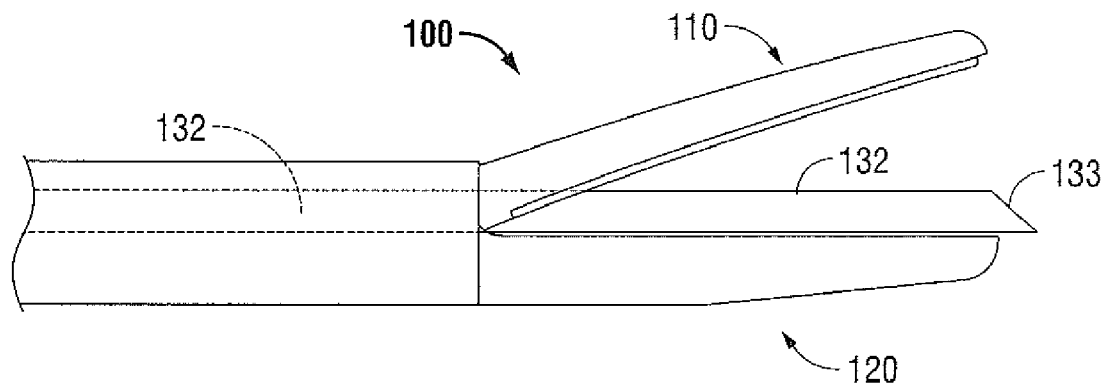
FIG. 5D is an enlarged, side view of the end effector assembly of FIG. 1 according to another embodiment of the present disclosure.

In another embodiment shown in FIG. 5D, cutter 132 is configured to be advanced distally such that at least a portion thereof is disposed distal to a distal end of jaw members 110, 120. In this scenario, cutter 132 may be embodied as a hollow hypodermic needle operably coupled to a fluid source (not shown) such that fluid may be injected from cutter 132 into tissue. For example, cutter 132 may be used to inject a nerve block agent into a desired tissue location prior to and/or during a surgical procedure (e.g., a polypectomy) to reduce pain. In another scenario, cutter 132 may be embodied as a conductive wire or rod and operably coupled to the same source of electrosurgical energy as forceps 10 or an alternative source of electrosurgical energy. In this manner, cutter 132 may be configured to operate as a monopolar electrode and used to cauterize tissue, for example, as a follow up to tissue sealing and/or cutting. Further, cutter 132 may be selectively energizable by the surgeon during cutting. In this way, the surgeon may electrosurgically cut the tissue along the tissue seal. As a result, cutter 132 may be substantially dull and still be employed to electrosurgically cut tissue.

As best shown in FIG. 3A, jaw member 120 may include a series of stop members 750 disposed on the inner facing surfaces of the electrically conductive sealing surface 122 to facilitate gripping and manipulation of tissue and to define a gap "G" (FIG. 4) between opposing jaw members 110 and 120 during sealing and cutting of tissue. Pivoting jaw member 110 pivots about pivot pin 103 to the closed position such that conductive sealing surface 112 engages stop members 750. The series of stop members 750 may be employed on one or both jaw members 110 and 120 depending upon a particular purpose or to achieve a desired result. A detailed discussion of stop members 750 as well as various manufacturing and assembling processes for attaching and/or affixing the stop members 750 to the electrically conductive sealing surfaces 112, 122 are described in commonly owned, co-pending U.S. Patent Publication Application No. 20040122423 entitled "VESSEL SEALER AND DIVIDER WITH NON-CONDUCTIVE STOP MEMBERS" by Dycus et al.

Figure 6E:
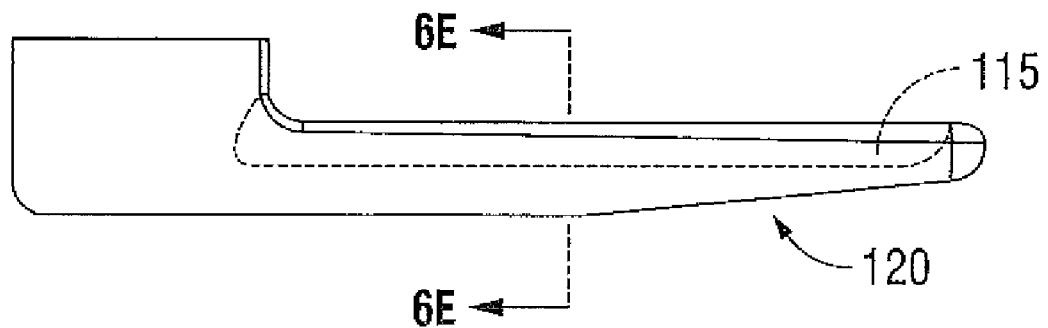
FIG. 6E is a side view of the workpiece of FIG. 6A with a section removed.
Figure 6F:
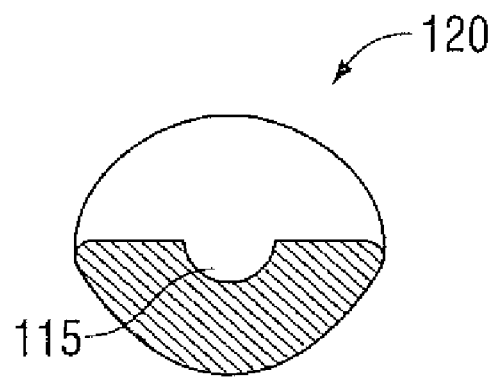
FIG. 6F is a cross-sectional view taken along section line 6E-6E of FIG. 6D.

FIGS. 6A-6F illustrate a method of manufacturing a jaw member including a knife channel. For purposes of illustration, the method illustrated in FIGS. 6A-6F is discussed with reference to jaw member 120 and knife channel 115 as substantially described above with respect to the other embodiments. In FIGS. 6A and 6B, a substantially cylindrical machined steel workpiece 125 is shown. Utilizing a suitable drilling device and corresponding drill-bit, a knife channel 115 is drilled a predetermined distance through at least a portion of the longitudinal thickness of the workpiece 125. In some embodiments, knife channel 115 may be drilled at a predetermined position with respect to the diameter of the workpiece 125 (e.g., the center point). As shown in FIGS. 6C and 6D, the drilling of knife channel 115 may be initiated at either end of workpiece 125 and subsequently drilled toward the end opposing the end through which drilling was initiated. Once knife channel 115 is drilled into workpiece 125, a section 125' of workpiece 125 is cut and removed from the workpiece 125' to generate jaw member 120, as shown in FIGS. 6C-6F. More specifically, a longitudinal cut 127a through a portion of workpiece 125 substantially bisects knife channel 115 along at least a portion of its length and intersects a cross-sectional cut 127b through workpiece 125 such that section 125' may then be separated from workpiece 125. As shown in the cross-section of FIG. 6E, knife channel 115 is substantially semi-circular in shape. In the illustrated embodiment, knife channel 115 is drilled into workpiece 125.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:
    a housing having a shaft that extends therefrom including an end effector assembly at a distal end thereof, the end effector assembly having a pair of jaw members movable between an open position wherein the jaw members are disposed in spaced relation relative to each other and a closed position wherein the jaw members cooperate to grasp tissue therebetween;
    a knife assembly including a cutter having a generally circular cross-section and configured to cut the tissue when the jaw members are in the closed position;
    at least one electrically conductive tissue sealing plate disposed on each of the jaw members, the electrically conductive tissue sealing plates adapted to connect to an electrosurgical energy source configured to deliver electrosurgical energy to tissue held between the jaw members to effect a tissue seal;
    a knife channel spirally disposed through at least one of the jaw members to define a substantially helical shape, wherein the cutter is configured to reciprocate within the knife channel when the jaw members are in the closed position to divide tissue grasped therebetween; and
    an actuator operably coupled to the knife assembly and configured to selectively reciprocate the cutter through the knife channel to divide tissue.

2. A bipolar forceps according to claim 1, wherein each jaw member includes a knife channel spirally disposed therethrough configured to substantially align with each other to define a substantially helical shape such that the cutter is configured to snake through the substantially helical shape when the jaw members are in the closed position to divide tissue grasped therebetween.

3. A bipolar forceps according to claim 1, wherein the actuator comprises at least one of a trigger and a movable handle operably coupled to the housing.

4. A bipolar forceps according to claim 1, wherein the knife assembly is operably coupled to the electrosurgical energy source such that the cutter is configured to be selectively energized to electrosurgically divide tissue.

5. A method for performing an electrosurgical procedure, the method comprising the steps of:
    providing an electrosurgical apparatus, including:
        a housing having a shaft that extends therefrom including an end effector assembly at a distal end thereof, the end effector assembly having a pair of jaw members movable between an open position wherein the jaw members are disposed in spaced relation relative to each other and a closed position wherein the jaw members cooperate to grasp tissue therebetween;
        a knife assembly including a cutter having a generally circular cross-section and configured to cut tissue along the tissue seal when the jaw members are in the closed position;
        at least one electrically conductive tissue sealing plate disposed on each of the jaw members, the electrically conductive tissue sealing plates adapted to connect to an electrosurgical energy source configured to deliver electrosurgical energy to tissue held between the jaw members to effect a tissue seal;
        a knife channel spirally disposed through at least one of the jaw members to define a substantially helical shape, wherein the cutter is configured to reciprocate within the knife channel when the jaw members are in the closed position to divide tissue grasped therebetween; and
        an actuator operably coupled to the knife assembly and configured to selectively reciprocate the cutter relative to the jaw members to divide tissue;
    delivering electrosurgical energy from the electrosurgical energy source to the electrically conductive tissue sealing plates to achieve a desired tissue effect; and
    actuating the cutter to selectively separate at least a portion of the effected tissue from the rest of the effected tissue.

6. A method according to claim 5, further compromising the step of:
    snaking the cutter through the knife channel when the jaw members are in the closed position.

7. A method according to claim 5, further comprising the step of:
    selectively energizing the cutter to electrosurgically divide tissue.

* * * * *